United States Patent
Gaillon et al.

(10) Patent No.: US 6,723,554 B1
(45) Date of Patent: Apr. 20, 2004

(54) APPARATUS AND METHOD FOR MEASURING OPTICAL PROPERTIES BY FEEDBACK CONTROL

(75) Inventors: Laurent Gaillon, Paris (FR); Robert Longin, Vanves (FR); Thanh Dung Luu, Montigny le Bretonneux (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/554,110

(22) PCT Filed: Nov. 26, 1998

(86) PCT No.: PCT/FR98/02542

§ 371 (c)(1),
(2), (4) Date: May 26, 2000

(87) PCT Pub. No.: WO99/27349

PCT Pub. Date: Jun. 3, 1999

(30) Foreign Application Priority Data

Nov. 26, 1997 (FR) ............................................ 97 14864

(51) Int. Cl.[7] ................................................ C12M 1/34
(52) U.S. Cl. ................................. 435/288.7; 422/82.05; 356/300; 356/317; 356/318; 356/337; 356/432; 356/445; 356/451
(58) Field of Search ......................... 422/82.05, 82.09; 435/286.1, 288.7; 250/458.1; 356/300, 432, 445, 317, 318, 337, 451

(56) References Cited

U.S. PATENT DOCUMENTS 3,731,806 A * 5/1973 McCormick ................ 210/94
4,058,363 A * 11/1977 Silbert ......................... 422/36
4,447,150 A * 5/1984 Heinemann ................. 356/41
4,622,468 A * 11/1986 Stefanski et al. ........ 250/458.1
4,740,356 A * 4/1988 Huber .......................... 422/81

FOREIGN PATENT DOCUMENTS

| EP | 0303524 | * 2/1989 |
| WO | WO 92/07245 | * 4/1992 |
| WO | WO 92/13482 | * 8/1992 |

* cited by examiner

*Primary Examiner*—David A. Redding
(74) *Attorney, Agent, or Firm*—Oblon, Spivak, McClelland, Maier & Neustadt, P.C.

(57) ABSTRACT

The invention concerns an apparatus and a method for measuring at least one optical characteristic, which can include in particular turbidity (T), absorbance (A) and fluorescence (F), of a medium (1), and a micro-bioreactor, a connector and associated male and female parts. The apparatus comprises a light source (3) provided with means for controlling (6) the intensity of the beam transmitted (11) by the source, a photodetector (4) for measuring the intensity of the beam reflected (12) by the medium, a feedback regulating system (7) operating on the control means such that the measured intensity of the reflected beam is equal to a predetermined nominal intensity, and means for reading the transmitted beam intensity, said intensity representing the medium optical characteristic(s). The apparatus also comprises means for adjusting the nominal intensity, such that the transmitted beam stabilised intensity is within a predetermined range. The invention is applicable to micro-bioreactors.

18 Claims, 7 Drawing Sheets

APPARATUS AND METHOD FOR MEASURING OPTICAL PROPERTIES BY FEEDBACK CONTROL

The present invention relates to an apparatus and a method for measuring the optical properties of a medium, and a corresponding micro-bioreactor. These optical properties may in particular include the turbidity, the absorbance and the fluorescence of the medium, at one or more wavelengths or over predetermined spectral ranges.

In many biological laboratories and also in certain industries, it is very often necessary to cultivate micro-organisms in liquid medium and to measure the concentration of the cells at different stages of the culture. This quantification may be performed directly on samples, by counting the cells or by measurement of the dry weight. These methods, although very accurate, are long and tedious, and it is more convenient to evaluate the quantity of the cells indirectly, for example by measuring the disappearance of substrates or the appearance of intracellular (NADH, etc.), or extracellular compounds (alcohols, organic acids, etc.). However, the most convenient and most frequently used methods for evaluating the cell concentrations of cultures are based on their optical properties.

When matter is struck by electromagnetic radiation, this interacts with the electronic charges of the atoms: part of the radiation passes through the matter without change of direction (transmitted radiation) and part is diffused in all directions, each illuminated particle then behaving as a light source. The quantity of light diffused by the particles present in the liquid medium increases with the number and size of these particles; in addition, in the case where the particles are micro-organisms, it has been shown that the diffusion of the light does not occur homogeneously in all directions, but predominantly in a direction close to that of the incident beam.

It is these diffusion phenomena which cause liquid micro-organism cultures to have a cloudy appearance, whose density increases with the cell concentration. Devices which can quantify this cloudiness, or turbidimeters, measure the turbidity of these cultures.

Existing turbidimeters may be divided into discontinuous measurement devices, which are used to make repeated measurements of the light transmitted and/or reflected by a liquid medium, and on-line measurement devices, for which a turbidity measurement probe is inserted into the liquid medium and connected to a recording system.

Discontinuous measurement devices, such as nephelometers, colorimeters, spectrophotometers and mixed turbidimeters, cannot for the most part measure high turbidity levels. Their measurement range does not normally extend beyond 1000 NTU (Nephelometric Turbidity Units) and is most often much more limited. It is thus necessary to dilute the samples, which increases the risks of error and the work to be performed by the operator. In addition, the sampling itself is very restricting, since it requires the presence of the operator at regular intervals throughout the culture period. Some mixed turbidimeters have been designed to cover a wider turbidity range, but they are costly.

On-line turbidimeters, whose measurement range may be fairly wide, have the disadvantage of requiring large culture volumes (about 1 litre) because of the size of the probes introduced into the cultures, which limits their use within bioreactors. In addition, cultures in bioreactors are generally aerated and stirred, which generates numerous bubbles which interfere strongly with turbidity measurement. These devices are also costly.

International patent application WO-92/13.482 discloses an apparatus and a method for measuring a blood parameter. The apparatus comprises a red light source and an infrared light source directing the light towards a blood sample and a detector receiving the light generated by the two sources and reflected by the blood. An optical feedback loop is used for each of the two sources so that the intensity of the light received by the detector is approximately constant for a range of values of the blood parameter, which allows precise control of the light sources. Reference curves are used to calculate two blood parameters from the feedback signals obtained respectively for each of the two sources.

A disadvantage of this technique is that it is in particular limited by the transmission capacities of the light sources and thus only covers a restricted measurement range with sufficient sensitivity. In addition, obtaining each result requires a stabilisation time which prevents rapid measurement. A serial analysis of a large number of samples, or measurement in heterogeneous media and /or media containing gas bubbles thus proves very difficult, or even impossible. In addition, inaccuracies can be generated during the processing of the feedback signals, because of the drift of capacitance values.

U.S. Pat. No. 4.447.150 relates to a device and a method for measuring blood properties and parameters, used to measure the oxygen saturation level of the blood. The apparatus disclosed comprises two light sources transmitting respectively at two distinct wavelengths and a detector measuring the light generated by the two sources and reflected by the blood. The light reflected or transmitted by the blood is maintained at a constant level by means of an optical feedback loop. In addition, the ratio of the two voltages corresponding to the measured light levels from the two sources respectively gives the percentage of saturation of the blood oxygen.

This technique also has the disadvantage of only allowing a restricted measurement range, in addition to the disadvantages already mentioned for document WO-92/13.482.

The present invention provides a measurement apparatus and a method which do not have the above disadvantages, and thus allow measurements over different ranges of values while retaining good sensitivity.

The apparatus and method of the invention can also offer a high speed of measurement and good accuracy.

In particular, the object of the invention is an apparatus for measuring turbidity able accurately to measure the turbidity of microbial cultures over a wide range of values, which is reliable, easy to use, readily adaptable to micro-bioreactors, of small size and inexpensive.

A further object of the invention is an apparatus for measuring absorbance and an apparatus for measuring fluorescence, able to measure with the same advantages as cited above the molecular absorbance and/or fluorescence of a medium, and, more generally, the invention provides an apparatus for measuring one or more optical properties of a liquid or solid medium.

The invention relates to a measurement apparatus as described above which is advantageously automated, so that experiments may be performed over a long time period without the presence of an operator.

Another object of the invention is a measurement apparatus as described above suitable for a battery of micro-bioreactors, making simultaneous measurements for the different micro-bioreactors possible.

The invention also relates to a micro-bioreactor equipped with a measurement apparatus having the above properties.

A particular object of the invention is a micro-bioreactor having systems for supplying the culture medium and gas which are simple and reliable, protected from any external contamination and able to handle small culture volumes. The system similarly protects the external environment from contamination by the culture itself.

The invention also relates to a micro-bioreactor with automatic sampling at certain predetermined stages of turbidity, absorbance, and/or fluorescence, and a micro-bioreactor with automatic dilution for cyclic cultures.

A further object of the invention is a method for measuring optical properties which may include in particular turbidity, absorbance and fluorescence, making possible measurement over a wide range of values with good accuracy, reliability and reproducibility.

The invention may be applied in the fields of microbiology and biotechnology, and more generally for any measurement of turbid substances, for example for analysis and treatment of water, agricultural or industrial effluents or pollutants (turbidity measurement).

It may be also be applied to in vivo or in vitro measurement of fluorescence, and more precisely to measurement of the concentration of intra- or extracellular fluorescent compounds.

The object of the invention is thus an apparatus for measuring at least one optical property of a medium, comprising:

a light source which transmits a light beam of variable intensity towards and into the medium, detection means to measure the intensity of the beam modified by the liquid medium, means of controlling the intensity of the beam transmitted by the source, storage means which store a representative value of a nominal intensity of the modified beam, a feedback system linked to the control means, the detection means and the storage means, operating on the control means so that the measured intensity of the modified beam is equal to the nominal intensity, and means of reading the intensity of the transmitted beam, for the nominal intensity of the reflected beam, the intensity of the transmitted beam and the nominal intensity of the modified beam being representative of the optical property or properties of the medium.

According to the invention, the measurement apparatus comprises means for adjusting the nominal intensity, linked to the reading means and the storage means, designed to adjust the nominal intensity so that the stabilised intensity of the transmitted beam falls within a predetermined range.

The nominal intensity of the modified beam is adjustable. It is thus possible to adapt the measurement apparatus to a given range of turbidity, absorbance and fluorescence values. The choice of the nominal intensity results from a compromise. It must be as high as possible, so that the intensity of the transmitted beam varies strongly with the turbidity, absorbance and/or fluorescence, which gives high accuracy. However, the nominal intensity must also be sufficiently reliable to cover the whole of the desired range without the intensity of the transmitted beam exceeding a maximum transmission threshold of the source, causing its saturation and/or deterioration.

This apparatus may thus be used for measurements of different ranges of values, from very low to very high levels, while retaining optimal sensitivity. In contrast, in the prior art the measurement range is fixed and linked to the reference voltage used.

In particular, the apparatus makes turbidity measurements possible over a wide range of optical densities with good accuracy. It is thus possible to obtain without difficulty a range extending from 45 to more than 17 000 NTU, which for a suspension of *Saccharomyces cerevisiae* yeast corresponds respectively to from 0.2 to 75 units of optical density (OD) at 600 nm with an error of about 2%. This apparatus also has good reliability and good reproducibility of measurements, corresponding to a low dispersion of values. Correspondence curves between turbidities and cell concentrations may easily be constructed for different organisms.

In addition, the measurement apparatus according to the invention may be manufactured at low cost, since it makes use of a relatively small number of inexpensive electronic components.

The storage means are advantageously designed to store a saturation intensity and the adjustment means regulate the nominal intensity to a lower value when the stabilised intensity of the transmitted beam is higher than the saturation intensity.

The values taken for the nominal intensity are advantageously predetermined.

The adjustment of the nominal intensity is thus automated, which in particular allows the developing turbidity of a medium to be monitored, over a wide turbidity range and with very good accuracy. It is particularly advantageous to use a luminescent diode, preferably transmitting in the infrared around 880 nm, for this automated adjustment. The voltage applied to the terminals of the transmitting diode during the transmission of the light beam in fact increases proportionately with the turbidity, thus giving excellent measurement accuracy.

The medium studied may be liquid or solid (gels, microscopy preparations).

The optical property or properties measured are advantageously selected from amongst the turbidity T, the absorbance A or the fluorescence F of the medium, for a given couple of transmission and reception spectra. Different embodiments of the invention include the following different combinations of the types of transmitted and received light:

monochromatic or wider band light source, detection at a corresponding wavelength (monochromatic or wider band), monochromatic or wider band light source, detection at another wavelength (case of fluorescence), polychromatic or wider band light source, detection at several corresponding wavelengths, white light source, detection at one or more wavelengths selected by filters.

The detection of the intensity of the beam received at several wavelengths can give additional information on the medium.

The light source is composed of a transmitter such as for example a diode, laser, coupled or not with an optical fibre, designed to transmit monochromatic light, light at spectral bands, possibly with variable widths, or white light. The transmission may be in the UV, visible, or near or far-infrared regions.

The detection means advantageously consist of one or more photodetectors, such as for example diodes (phototransistor, photodarlington) or photoelectric cells, each having monochromatic or a wider passband reception, in the UV, visible, or near or far-infrared regions. In the case of infrared measurements, the detection means are advantageously insensitive to visible light, for convenience.

The language "beam modified by the medium," and similar terminology appearing in the specification and claims should be understood to mean a beam transmitted through the medium without interaction, a diffused or reflected portion of a beam entering the medium, or a beam transmitted after interaction with the medium (in the case of fluorescence, for example).

The detection means are placed at one or more appropriate angles with respect to the direction of the transmitted beam, preferably at about 180° (necessarily at about 180° for transmission).

The beam incident on the medium is preferably parallel. This gives a very good ratio of modified light to transmitted light.

Each wavelength measured is preferably selected so as to give information on a distinct type of particle.

Thus, for turbidity measurements, two distinct wavelengths lead to results on particles of two different sizes coexisting in suspension. These might for example be cells infected by phage particles and phages liberated by the lysed cells. For a given type of particle, the quantity of light diffused or transmitted depends on the wavelength detected. In addition, the higher the wavelength, the higher the transmitted light/transmitted light ratio.

An embodiment for measurement at two wavelengths consists of transmitting using two transmitters of different wavelengths, for example infrared and visible. Another embodiment consists of transmitting white light and placing filters on the detector so as to select the two wavelengths.

For absorbance measurements, reception of two distinct wavelengths allows quantification of two types of molecules absorbing at two distinct wavelengths, or the correlation of observations on a type of particle.

In general, measurements at several wavelengths can be used to determine the proportion and nature of the particles, cells or molecules in the media analysed, and to distinguish their size, shape, concentration, nature and/or the proportion of different cell, particle or molecular species. If the number of wavelengths is equal to n, a mathematical process may be performed using a system of n equations with n unknowns.

The nominal intensity (fixed intensity of the modified beam) is advantageously selected as a function of the range of concentration of the particles to be measured in the medium, the nominal intensity decreasing when the concentration range to be measured increases.

The measurement apparatus according to the invention does not simply measure the light modified by a liquid medium to determine the turbidity, absorbance, or fluorescence, but the energy supplied by the source in order to obtain a fixed quantity of modified light. This energy, or intensity of the transmitted beam, gives the turbidity, the absorbance or the fluorescence of the liquid or solid medium, for each wavelength measured, by means of a simple mathematical relation established by calibration curves. Thus, when the light source transmits an infrared light around 880 nm, the quantity of energy transmitted by the medium is inversely proportional to the turbidity of the medium passed through and the electronic feedback system automatically adjusts the transmitted beam so that the modified light is equal to a fixed value.

In the case of fluorescence measurement, the quantity of light modified is proportional to the intensity of the transmitted beam and to the concentration of the fluorescent substance. It is also affected by internal filter phenomena.

The measurement apparatus also obviates any removal of portions of the medium other than for analysis samples, which simplifies handling operations, avoids error risks during dilution after sampling and reduces the risks of contamination of the culture or the environment (for example in the case of pathogen cultures).

The measurement apparatus may advantageously be completely outside the liquid medium. Thus, in the case where the medium comprises a culture, the apparatus does not have to be sterilised and is not liable to deterioration by fouling or coating with biofilms.

The measurement apparatus is preferably automated, in particular by automatic recording of data and by automatic adjustment of the nominal intensity of the modified beam. It is thus possible to perform long experiments without the presence of an operator, in particular for monitoring cultures on a 24-hour basis without human supervision.

Another advantage of the measurement apparatus is its capacity to be adapted to a wide variety of liquid media, and in particular to continuous cultures of all types, such as for example chemostat, turbidostat or cyclic cultures.

The light source and/or the detection means are preferably designed to measure the intensity of the modified beam around at least one wavelength, the optical property or properties of the medium each corresponding to a wavelength or wavelengths.

In a first preferred embodiment, the optical property or properties of the medium comprise(s) the turbidity of the medium.

The detection means are thus preferably arranged in the direction of the transmitted beam, the received intensity/transmitted intensity ratio being optimal. In an alternative of the embodiment, at least some of the detection means are arranged at an angle to the direction of the transmitted light, so as to detect the diffused light.

In the first embodiment, the light source and/or the detection means are preferably designed for infrared measurements, advantageously around 880 nm.

It is for example advantageous that the light source is a luminescent diode or LED, transmitting in the infrared.

The transmission of infrared light with wavelengths varying from 840 to 920 nm with a peak at 880 nm simplifies the use of the measurement apparatus and gives good accuracy. Since the diffusion of the light depends on the wavelength, the use of white light, for example, makes the apparatus more difficult to use and gives less accurate results than an almost monochromatic infrared light. In addition, the infrared radiation passes more easily through the matter, which is favourable for the measurement of high turbidities. Transmission at other wavelengths or of white light is however also possible.

In a second preferred embodiment, the optical property or properties of the medium comprise(s) the absorbance of the medium, the invention thus applying to the colorimetry and the spectrophotometry of a liquid or solid medium.

In a third preferred embodiment, the optical property or properties of the medium comprise(s) the fluorescence of the medium.

Thus, the GFP (Green Fluorescence Protein) naturally present in the *Aequora victoria* jellyfish, when excited by UV or blue light (2 excitation peaks at 395 and 475 nm), transmits green light at different wavelengths (509 and 540 nm) by fluorescence, which allows distinction between the incident and diffused light. The transmission does not require the presence of a substrate or cofactor. There are different versions of the gene coding for this protein, which has the effect of improving its quantum yield and modifying its emission spectrum (HELM, R., Nature, vol. 373, pp. 663–664, 1995).

Similarly, it is possible to quantify the intracellular or extracellular compounds transmitting by fluorescence. For example:

| Fluorophore | Excitation wavelength | Fluorescence wavelength (transmission) |
|---|---|---|
| NADH, NADPH | 350 | 450 |
| FAD | 450 | 520 |
| Aromatic amino acids | 275 | 310 |
| Tryptophan | 289 | 330–360 |
| Nucleotides | 280 | 375 |
| Riboflavins | 445 | 520 |
| Pyridoxine | 313 | 385–415 |
| Antibiotics | variable | variable |
| F (420) | 425 | 472 |

Thus the oxido-reduction Coenzyme NADH transmits a fluorescence at 450 nm when it is excited by light at wavelength 350 nm (the oxidised form NAD does not fluoresce). During cell growth, the quantity of NADH varies with the cell concentration (Li, J., Biotechnology and Bioengineering, vol. 37, pp. 1043–1049, 1991).

The same is true for different fluorescent colorants and chromophores (also called fluorochromes or fluorophores), such as fluorescein, fluorescent antibodies, pigments, quinine, etc.

The introduction into different cells (prokaryotes or eukaryotes) of genes coding for GFP and their expression under different conditions thus allows the fluorescence to be continuously monitored. The measurement apparatus according to the invention may also be used to study the internal filter effects of fluorescent media.

This third embodiment has applications in many fields, such as the quantification of fluorescent substances in gels, blots or microplates. In addition, in vivo studies are possible, such as the measurement of gene expression by monitoring the fluorescence of tagged proteins for which they code, leading to both the quantification and cellular localisation of these proteins. These measurements performed in bioreactors can also be used to carry out analyses as a function of time, the physiological state of the cells, and the environmental conditions of the culture.

The measurement apparatus preferably comprises a processing unit linked to the reading means and having storage means, the storage means being designed to store at least one equation determined by a calibration curve giving the optical property or properties of the medium as a function of the intensity of the transmitted light beam for respectively at least one value of the intensity of the modified beam. The processing unit then calculates the optical property or properties of the medium from the stabilised intensity of the transmitted light beam for one of the values of the nominal intensity, on the one hand, and the equation corresponding to this value of the nominal intensity, on the other.

The determination of the turbidity, the absorbance and/or the fluorescence of the medium from these measurements is thus automated, and may be performed in real time.

It is thus advantageous that the processing unit comprises a central processing unit and at least one card for analog/digital and digital/analog conversion, coupling the central processing unit to the control means and the regulation means.

Such cards make current/voltage and voltage/current converter stages unnecessary.

In addition, the processing unit preferably calculates the optical property of the medium directly from a value proportional to the intensity of the transmitted beam.

This embodiment contrasts with known techniques, in which the optical properties are obtained from feedback signals, which must pass through an integration system to be processed. It thus avoids the introduction of inaccuracies in the results.

Advantageously, the measurement apparatus comprises a clock, recording means in the means of storage of representative values of the optical property or properties of the medium, and means of repeated activation of the feedback system and the recording means.

The recording of the results is thus automated, the measurements being advantageously performed at regular intervals so that the variation of the optical property as a function of time can be monitored. In a first embodiment, the values recorded are those directly obtained by reading the intensity of the transmitted beam, these results being processed subsequently. In a second embodiment, the measurement apparatus determines the optical properties after each measurement, and it is these which are recorded in the storage means.

The feedback regulating system and the control means are such that the equalisation of the measured intensity and the nominal intensity of the modified beam is obtained continuously.

Thus, the response time is negligible and only limited by the intrinsic response times of the electronic components, of the order of nanoseconds. This embodiment contrasts with known techniques, in which the adjustment is made by successive trials and governed by periodic impulses. The measurement apparatus can thus offer a high speed of measurement, which can be applied for example in the serial analysis of a very large number of samples and to perform measurements in media which are heterogeneous or perturbed by gas bubble circulation. In these latter cases, the measurement apparatus is equipped with means for performing measurements in bursts, and for carrying out statistical analysis of values collected from each of these bursts, so as to calculate significant values.

A further object of the invention is a micro-bioreactor, equipped with a measurement apparatus according to the invention.

The fact that the measurement apparatus can be completely outside the micro-bioreactor, that it does not require sample removals and corresponding dilutions, and that it enables automation of measurements, enables the construction of a micro-bioreactor with considerable advantages. In particular, a small volume of the culture is sufficient for measurements, which improves the ease of use. The small size and the low frequency of changes of supply vessels for the culture media are other advantages. In addition, the micro-bioreactor and its systems for supplies and removal of effluents may be completely isolated from the external media. Their pressurisation ensures simplicity and reliability, since the use of pipes with known head-loss gives precise flow rates and avoids costly and bulky pumps. This guarantees sterility by preventing any contamination of the supply vessels by the culture and of the culture by the external environment, and allows for example the culture of pathogenic strains in complete safety.

The automation of the measurements also makes possible the automation of sampling for optical densities corresponding to exact physiological states, such as for example maximum growth rate, end of growth or end of stationary phase. It also enables the execution of automatic dilutions for cyclic cultures.

Another advantage is that several micro-bioreactors may be linked in a battery, independently or in cascade, each containing a culture in well-defined and reproducible conditions. The measurement apparatus linked to the different micro-bioreactors are then advantageously linked to a central system designed to control the measurements in parallel.

In a preferred embodiment, the micro-bioreactor comprises:
- a tube closed by a stopper, intended to contain a culture,
- a first pipe, to inject sterile air and the culture medium into the culture, and
- a second pipe, to remove the effluents, the tube and all the pipes being under pressure.

In an advantageous embodiment for cyclic cultures, the micro-bioreactor comprises a dilution system designed to dilute a culture. The measurement apparatus thus comprises a clock and a processing unit linked to the dilution system, the processing unit cyclically triggering the dilution system.

This device is very advantageous for developing strains or for performing physiological studies on the growth parameters such as, for example, the level and yield of growth or measurement of the latency time before the resumption of growth.

The processing unit preferably repeatedly activates the feedback system, records the representative values of the optical property or properties of the medium in the storage means, and triggers the dilution system when it observes a stagnation of the optical property or properties of the medium over a plurality of the latest recorded values.

In alternative embodiments, the processing unit triggers other actions on the medium, such as for example the supply of various solutions or gases, when it observes stagnation.

In another embodiment, the processing unit periodically triggers the dilution system, after a predetermined culture period.

The invention also relates to any system equipped with a measurement apparatus according to the invention, such as for example a bioreactor (adaptation by increasing or internal), an independent apparatus or a microplate reader.

Different types of cultures may also be used: discontinuous (batch) cultures, optionally with continuous or sequential addition of one or more substrates (fed batch); cyclic cultures; turbidostat, enabling the maintenance of a culture turbidity at a constant value by addition of a constant volume of the culture medium into the bioreactor, so that the turbidity oscillates around a reference value; or chemostat, enabling the continuous addition of a constant volume of the culture medium into the bioreactor at a rate lower than the maximum growth rate of the micro-organism.

Various methods of introduction of fluids may be used, such as for example pumps, all-or-nothing or proportional solenoid valves, flowmeters, several supply vessels for different substrates or compounds, added as a function of time or of the optical density and/or several gases.

The pipes are preferably connected by means of connectors each comprising a male part connected to a first pipe, a female part connected to a second pipe, and means of connection of the male part and the female part, each of these male and female parts comprising:
- a tapered and hollow end connected to the pipe corresponding to this part and communicating with this pipe, and
- a tapered sleeve, surrounding this end and connected to this pipe.

The end of the male part is introduced into the end of the female part, the sleeve of one of the parts is introduced into the sleeve of the other part and the sleeves are fixed to each other by connection means.

The sleeves thus serve to protect the ends, through which the fluid circulates.

The connectors are preferably provided with stoppers to give a sealing closure, and are sterilised with steam, in an autoclave for example. During the connection, the stoppers are removed and the ends of the sleeves are briefly passed over a flame to ensure, their sterility and that of the air in close proximity. This system enables the internal areas of the male and female parts to be kept cold and also permits immediate connection without deterioration of the seals, while retaining complete sterility.

The sealing of the connection between the two ends is advantageously obtained by means of seals attached to the male and female parts respectively and against which the ends of the female and male parts respectively are engaged.

The sleeve of the male part is advantageously introduced into the sleeve of the female part. The protection given by the sleeves is thus still more reliable.

In addition, it is advantageous that the connection means comprise a locking ring linked to the pipe corresponding to the receptor sleeve and a fixing system (for example a screw thread) on the sleeve introduced into the receptor sleeve and engaging this ring.

The locking ring is advantageously machined to include a stop limiting the locking. This embodiment avoids excessive compression of the seals which would cause their deterioration.

In another embodiment, O-ring sealing rings are added to the internal areas of the male and female parts. They reinforce the safety and sealing.

The invention also relates to a connector, and to the male and female parts of such a connector, particularly suited to the micro-bioreactor of the invention and corresponding to the above description.

A further object of the invention is a method for measuring at least one optical property of a medium, in which:
- a light beam of variable intensity is transmitted towards or into the medium,
- the intensity of the beam modified by the medium is measured,
- the intensity of the transmitted beam is adjusted so that the intensity of the modified beam is equal to a fixed nominal value,
- the stabilised intensity of the transmitted beam thus obtained is read, and
- a value representative of the stabilised intensity is related to an equation determined by a curve giving the optical property or properties as a function of the intensity of the representative value of the stabalised intensity of the transmitted beam for the nominal intensity of the modified beam, so as to calculate the optical property or properties of the medium.

According to the invention, the nominal intensity is adjusted so that the stabilised intensity of the transmitted beam is within a predetermined range.

Other advantages and objects of the invention will appear from the examples given below, which are illustrative and non-limiting, with reference to the attached figures in which.

Figures 4, 5:
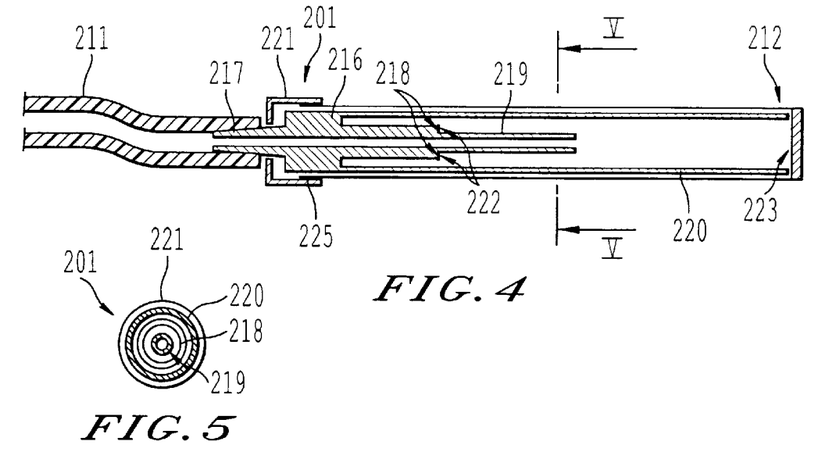
FIG. 4 represents a longitudinal section of the male part of a connector according to the invention, with stopper, used for the micro-bioreactors of FIGS. 2 and 3.
FIG. 5 is a cross-section along line V—V of the male part of FIG. 4.
Figure 11:
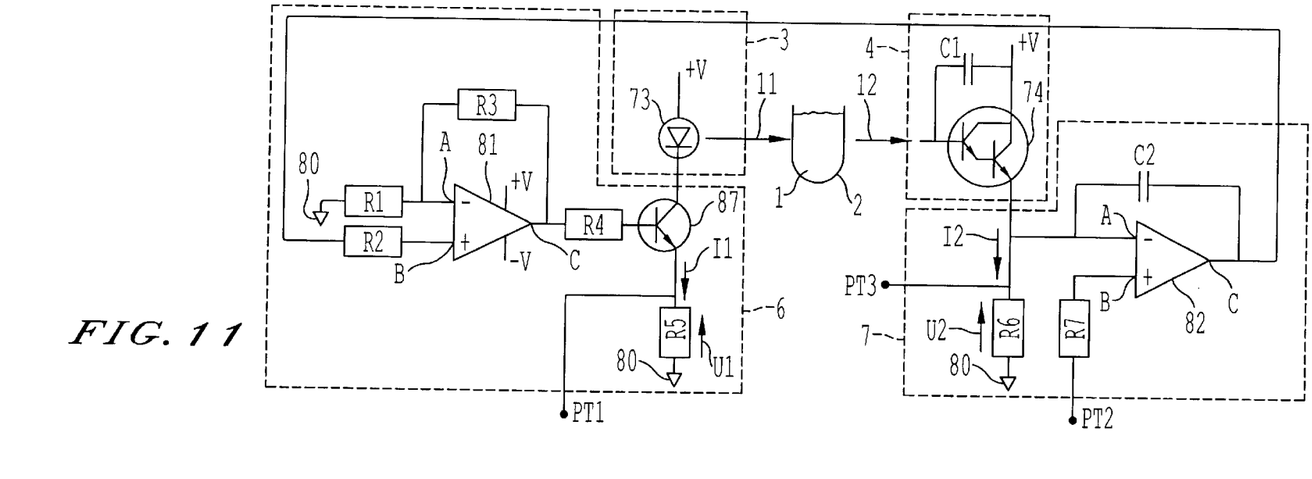
FIG. 11 illustrates a third electronic embodiment instead of those used in FIGS. 9 and 10.

The technical teaching of these figures, in particular FIGS. 4 and 11, is considered as an integral part of the description which follows.

Figure 9:
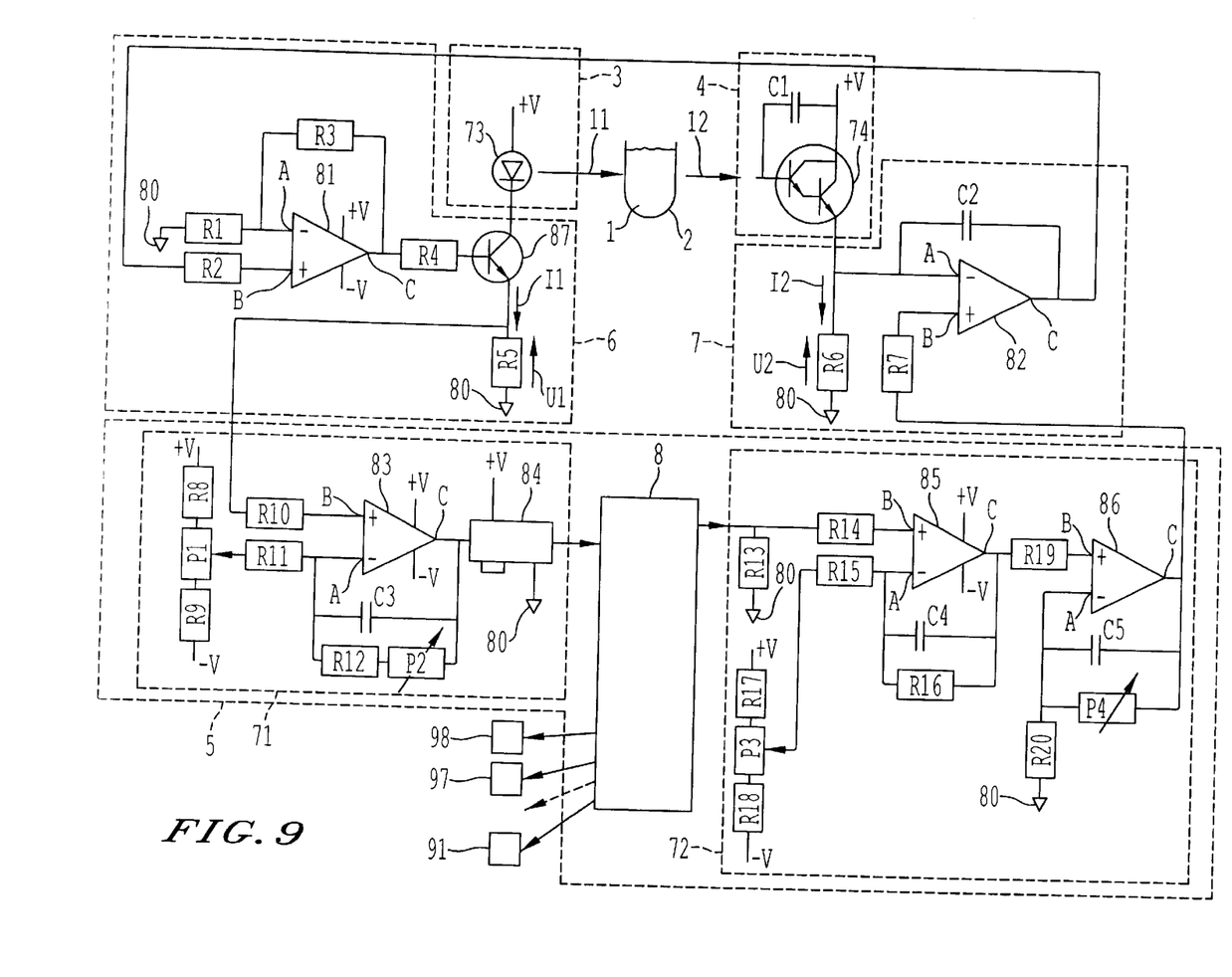
FIG. 9 represents a diagram of an embodiment of the electronics of a measurement apparatus according to the invention, applicable to the micro-bioreactor of FIG. 2 and the automatic station of FIG. 3.
Figure 10:
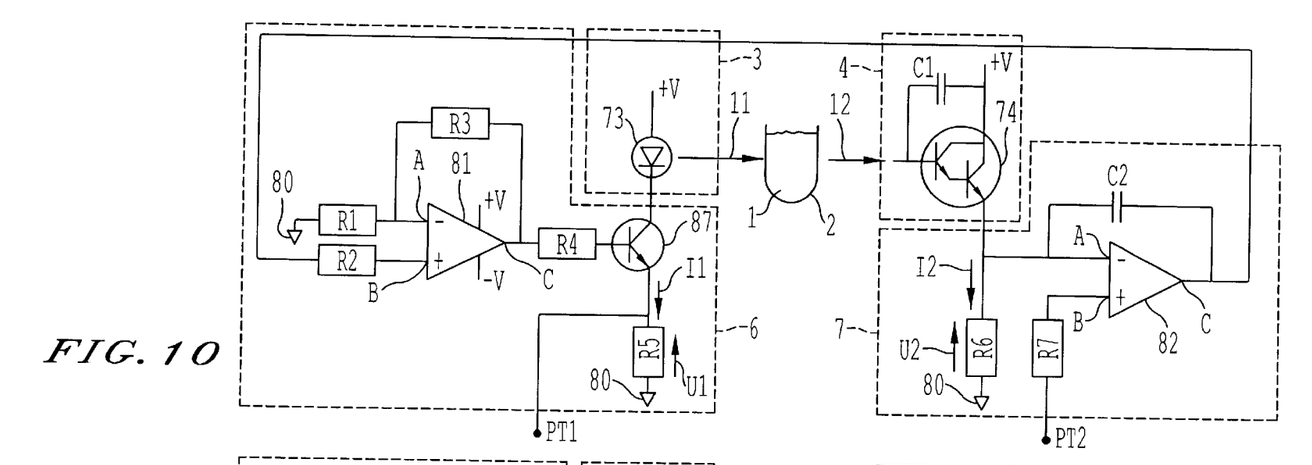
FIG. 10 illustrates a second electronic embodiment instead of that used in FIG. 9.

On FIGS. 9 to 11, identical components are identified by the same reference numbers.

An apparatus for measuring turbidity T (FIG. 1) of a liquid medium 1, contained in a transparent container 2, comprises a light source 3 which transmits a light beam 11 towards the medium 1. The light source is preferably nearly monochromatic and transmits in the infrared, for example around 880 nm.

Figure 1:
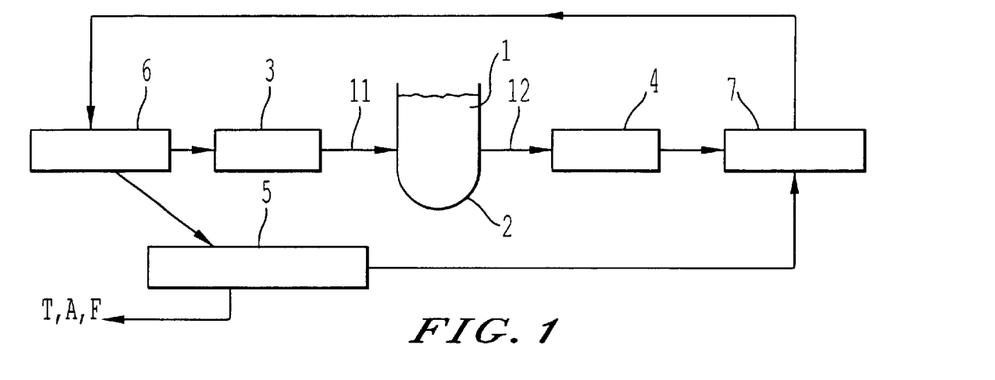
FIG. 1 is a block diagram of the measurement apparatus according to the invention.

The beam 11, after passing through the medium 1, becomes a modified beam 12 whose intensity is measured by a photodetector 4. The photodetector 4 is, for example, of the photodarlington type. The light source 3, the container 2, and the photodetector 4 are preferably aligned. In the alternative embodiments, the photodetector 4 is not aligned with the light source 3 and the container 2, so that it detects a diffused or reflected beam. The preferred embodiment, however, corresponds to optimum accuracy.

The light source 3 is connected to a control unit 6, able to read and modify a voltage U1, directly proportional to the current I1 passing through the light source 3 and thus to the intensity of the transmitted beam 11. The representative values of the transmitted beam 11 and of modified beam 12 are preferably linearly proportional to the currents I1 and I2 passing through the light source 3 and the photodetector 4, respectively.

The regulating system (7), connected to the photodetector 4 and to the processing unit 5, is designed to compare a voltage U2, directly proportional to the current I2 passing through the photodetector 4, with a reference value V2. This later value, supplied by the processor unit 5, is representative of a nominal value of the modified beam 12 for a given measurement range.

The processing unit 5, may, in addition to data processing means, comprise in particular means for setting the value of the voltage V2 in the unit 7, means for reading the representative values U1 of the intensity of the transmitted beam 11, and means for storing the data. The regulating system 7 is also connected to the control unit 6 and acts on this as a function of the difference between the voltages U2 and V2. This feedback loop, to which units 3, 4, 6 and 7 contribute, thus has the function of reducing this difference to zero. At equilibrium, the voltage U2 is equal to the reference value V2 and the voltage U1 is stabilised at a value V1.

This voltage V1 is representative of the turbidity T of the medium 1. This voltage V1 is sent to the processing unit 5 which, for a given reference value V2, calculates the turbidity T from the voltage V1 using a mathematical function established from a calibration curve of the measurement apparatus giving the turbidity T as a function of the voltage V1 for the value V2.

Figure 12:
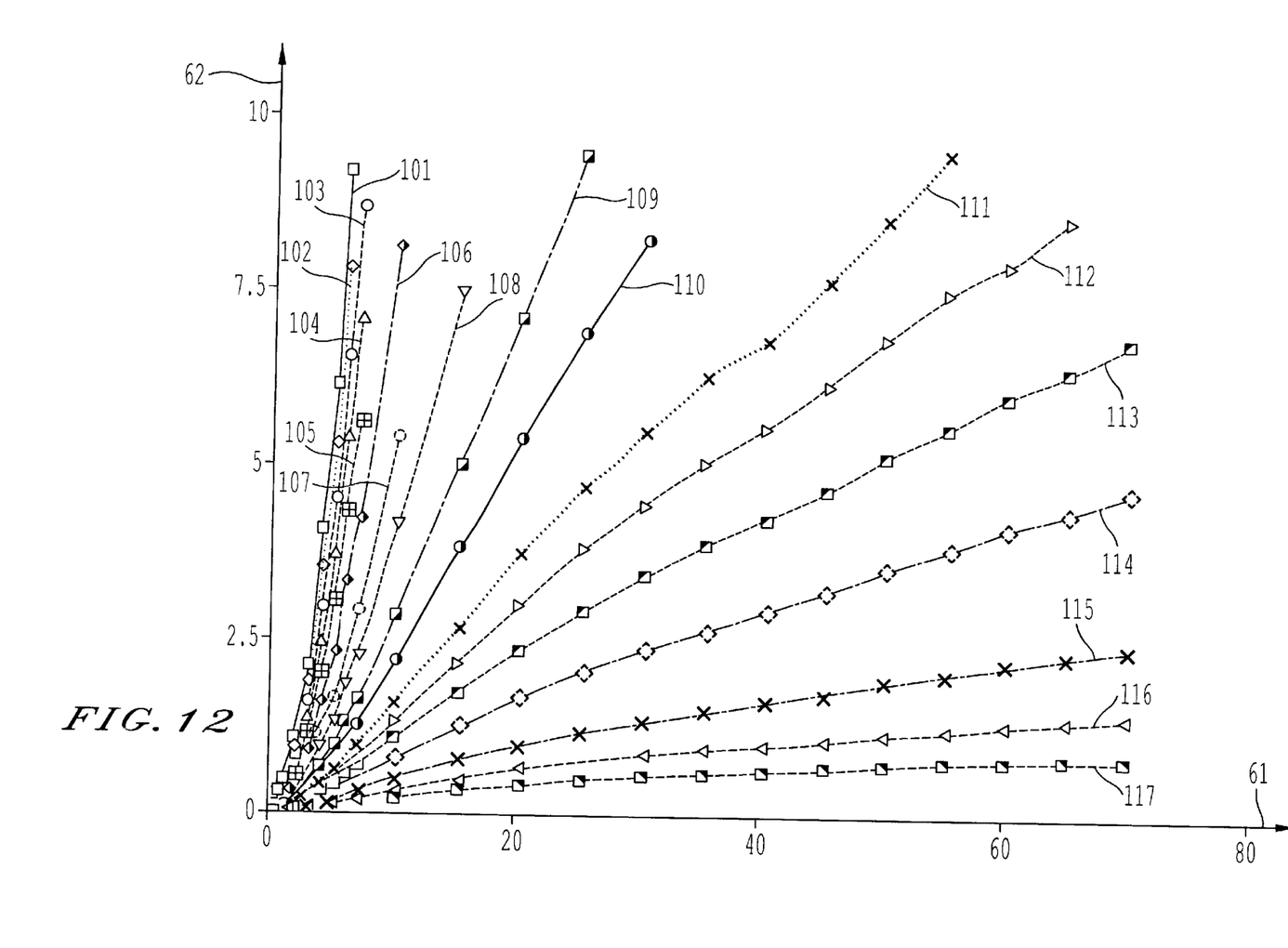
FIG. 12 represents a set of calibration curves prepared with a culture of *Saccharomyces cerevisiae* yeast, giving the representative voltage of the intensity of the transmitted beam as a function of the turbidity for a set of representative voltages of the transmitted beam nominal intensity.

A set of calibration curves 101–117 is thus given in FIG. 12 against a first axis 61 giving the turbidity T in OD units and a second axis 62 giving the stabilised voltage V1 in Volts. These calibration curves 101–117 correspond respectively to the following reference values V2: 8 V, 7 V, 6 V, 5 V, 4 V, 3 V, 2 V, 1.5 V, 1 V, 0.75 V, 0.5 V, 0.4 V, 0.3 V, 0.2 V, 0.1 V, 0.05 V, 0.025 V.

The choice of the reference value V2 depends on the turbidity range T which it is desired to cover. The higher the reference value V2, the more the stabilised voltage V1 increases rapidly with the turbidity T. Given that the voltage V1 has an upper limit, the value V2 cannot thus be maintained for a higher threshold corresponding to this turbidity range. For a given range, however, it is advantageous to select the reference value V2 to be as high as possible, so as to obtain the largest slope of the variation of the voltage V1 as a function of the turbidity T, and thus the best measurement accuracy.

The measurement apparatus preferably adjusts the reference value V2 automatically as a function of the measurements. To achieve this, it is advantageous to proceed as follows. The processing unit 5 is provided with an upper threshold of the voltage V1 and a list of values V2 which are predetermined and sorted in decreasing order. At the beginning of a series of measurements, the processing unit 5 transmits the highest value of V2 on the list to the regulating system 7, then the feedback loop adjusts the voltage U1 so that U2 is equal to V2. The value V1 of the voltage U1 is then sent to the processing unit 5, which verifies for each measurement that the stabilised voltage V1 remains less than the predetermined threshold voltage. If the voltage V1 exceeds this threshold, the processing unit 5 sends a lower reference value V2 to the regulating system 7, and this new reference value is adopted for the following measurements. In the case where a mathematical relation links the value V1 to the value V2 for several turbidity ranges, it is also possible to request the processing unit 5 itself to calculate the reference value V2 which is best suited for the turbidity calculation.

The measurement apparatus preferably determines the turbidity T automatically after each measurement. This determination is then performed by the processing unit 5 from the calibration curves 101–117.

Figure 2:
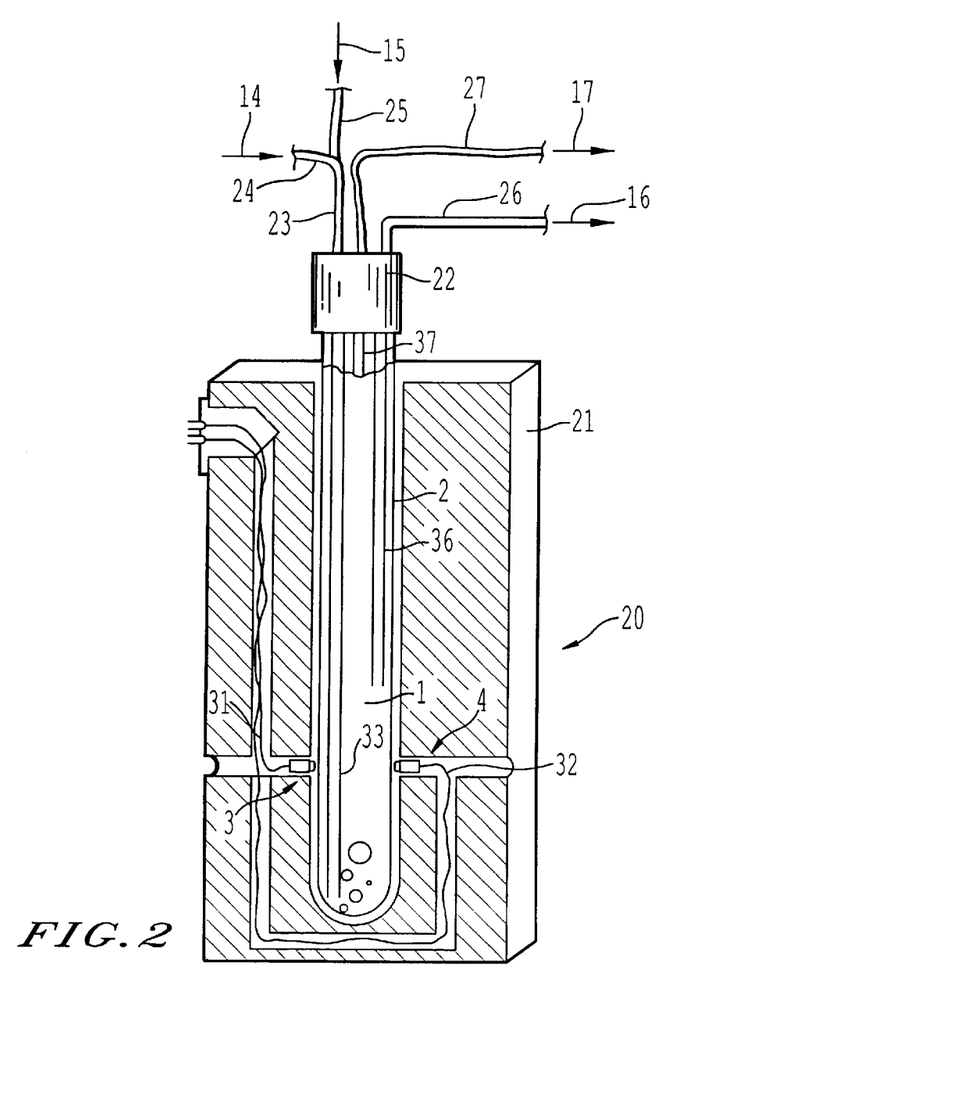
FIG. 2 represents a micro-bioreactor equipped with a measurement apparatus according to the invention.

The measurement apparatus is advantageously applied to a micro-bioreactor 20, as represented in FIG. 2. In the embodiment shown, the container 2 is a glass tube, for example of square section with 20 mm sides and 160 mm high, which gives a useful culture volume of about 55 to 60 ml. More generally, the glass tube 2 advantageously contains a useful volume of between 10 and 60 ml. The tube 2 is inserted in a metal alloy block 21, itself placed in a dry thermostated bath. The block itself may be provided with an independent heating system. The tube 2 is closed with a stopper 22, through which pass several small glass or plastic tubes or pipes. A first of these glass pipes, referenced 33, passes to the bottom of the tube 2, injecting a constant stream of sterile air or gas 14 into the culture. It may also, when required, be used to inject fresh culture medium 15. This glass pipe 33 is connected outside the tube 2 to a supply pipe 23 into which the supply pipes 24 and 25 feed, supplying respectively sterile air or gas 14 and culture medium 15. The pipes 24 and 25 are preferably provided with a solenoid valve. The micro-bioreactor 20 also comprises a second glass pipe 36 which emerges in the middle of the tube 2 and which is used for inoculation and sample removal. The glass pipe 36 is connected, outside the tube 2, to an extraction pipe 26 for removal of samples 16.

The micro-bioreactor 20 also comprises a third glass pipe 37, placed at the top of the tube 2, connected to an effluent carboy via a removal pipe 27, positioned outside tube 2, which is used to remove the effluents 17.

The external pipes 23–27 are preferably flexible.

The light source 3 and the photodetector 4 are inserted into openings in the metal alloy block 21, on either side of the tube 2, and are connected by electric cables 31 and 32 respectively to the measurement system.

The whole of the micro-bioreactor 20, with its external pipes 23–27 and the supply vessel supplying the culture medium 15 to the micro-bioreactor 20, are preferably under overpressure. In addition, the sterile air or gas 14 only circulates in one direction, preventing any contamination. The external pipes 24 and 25 are thus advantageously pipes with known head-loss, so that precise flow rates can be achieved. The whole assembly can be heat-sterilised and is completely sealed.

In a first embodiment, the turbidity measurement apparatus is applied to an isolated micro-bioreactor. In a second embodiment, illustrated in FIG. 3, a series of turbidity measurement apparatus is applied to a battery 40 of 8 micro-bioreactors. As an example, the battery 40 comprises 8 micro-bioreactors 41–48 of the type of the micro-bioreactor 20 described above. The series of external pipes 24, 25 and 27 of the micro-bioreactors 41–48 is then respectively coupled to three central pipes 54, 55 and 57. Each of these pipes 25 is provided with a solenoid valve 35. Similarly, each of the pipes 24 is provided with a solenoid valve 34.

Figure 3:
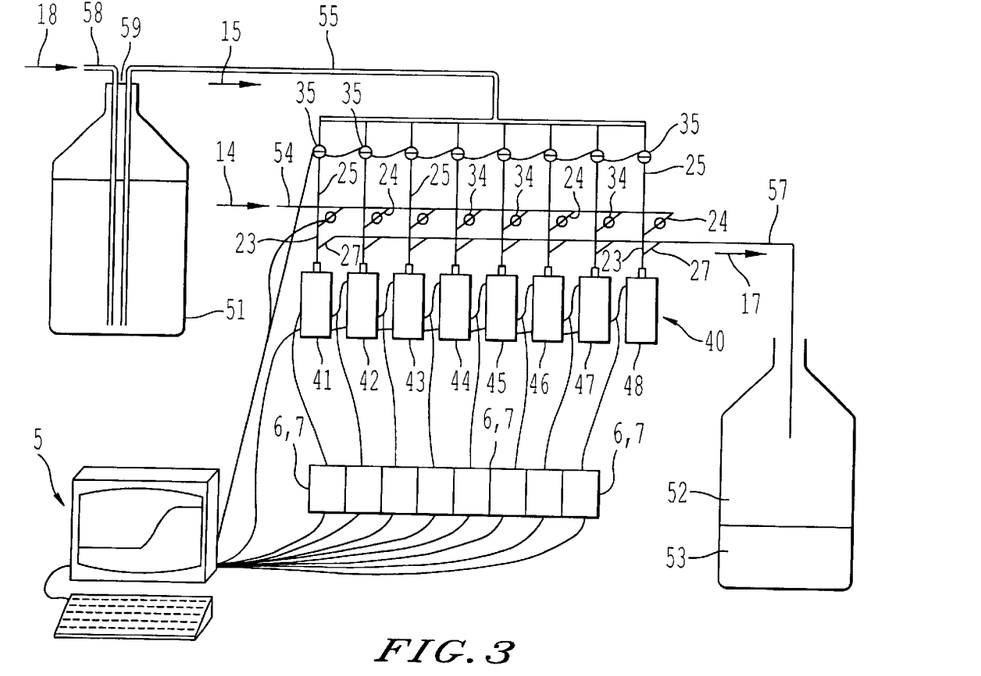
FIG. 3 shows an automatic station comprising eight micro-bioreactors according to the invention.

The pipes 27 may be provided with solenoid valves so as to enable automatic samplings. The pipe 57, to which the pipes 27 merge, emerges into an effluent carboy 52 intended to contain the waste 53.

The culture medium supply vessel 15, under pressure, comprises a container 51 closed by a stopper 59 and supplied with sterile air or gas 18 by a pipe 58 passing through the stopper 59 and emerging at the bottom of the container 51. The pipe 55 passes through the stopper 59 and emerges at the bottom of the container 51. This device may be used to adjust the pressure at the bottom of the supply vessel. This pressure is equal to the gas pressure in pipe 58, whatever the height of the liquid (Mariotte vessel).

The pipes 23–27, 33, 36, 37, 54, 55 and 57 are preferably connected by means of connectors 200, represented on FIG. 8 and described in detail below.

The connector 200 comprises
a male part 201 (FIGS. 4 and 5) connected to a first pipe 211 constituting one of the pipes and closed by a first stopper 212, and
a female part 202 (FIGS. 6 and 7) connected to a second pipe 214 constituting another of the pipes and closed by a second stopper 215.

The male part 201 comprises:
a body 216, preferably of stainless metal, connected to a pipe 211 by a part 217 which may be slightly tapered,
an internal shoulder 218,
an internal end 219,
a sleeve 220,
a threaded locking system 221 in ring form, and
a flat round seal 222 with a hole in its centre.

The stopper 212 of the male part 201 is provided with a flat round seal 223 at its end, and an end 225 provided with an external screw thread which engages with the locking system 221.

Figure 6:
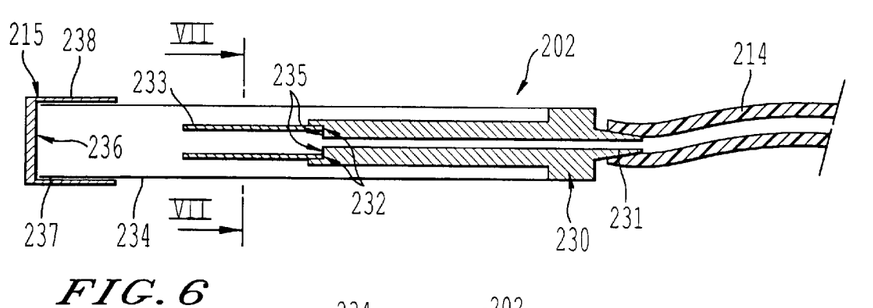
FIG. 6 is a longitudinal section of the female part of the connector corresponding to the male part of FIG. 4, with stopper.
Figure 7:
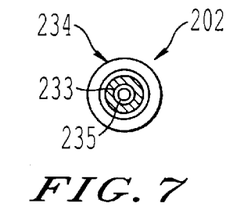
FIG. 7 is a cross-section along line VII—VII of the female part of FIG. 6.

The female part 202 comprises:
a body 230, preferably of stainless metal, connected to a pipe 214 by a part 231 which may be slightly tapered,
an internal shoulder 232,
an internal end 233,
a sleeve 234 with an end 237, provided with an external screw thread, and
a flat round seal 235 with a hole in its centre.

The stopper 215 of the female part 202 is provided with a flat seal 236 at its end, and an end 238 provided with an internal screw thread which screws onto the external end 237 of the sleeve 234.

Before connection, the male part 201 and the female part 202, connected respectively to pipes 211 and 214 and provided with their respective stoppers 212 and 215, are sterilised, for example by steam.

The connection is performed as follows:
the stoppers 212 and 215 of the male part 201 and female part 202 are unscrewed without removing them;
the ends 219 and 233 of the male part 201 and female part 202 are then placed over a flame, and the connectors are turned vertically, with the ends 219 and 233 at the bottom, so that the two stoppers 212 and 215 fall out;
the sleeves 220 and 234 are then passed rapidly through the flame;
the male part 201 is then introduced into the female part 202 until the end 219 engages with the seal 235 and the end 233 engages with the seal 222; and
the locking system 221 is screwed onto the screw thread of the end 238 of the sleeve 234.

Figure 8:
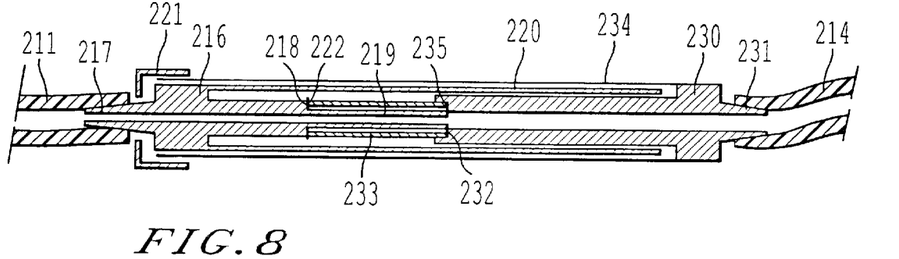
FIG. 8 shows the connector assembled from the male and female parts of FIGS. 4 to 7.

The connector 200 is thus assembled, giving a sealing and reliable connection, with protection by the sleeves 220 and 234 as represented in FIG. 8.

The light sources 3, photodetectors 4, control unit 6, and regulating system 7 and the solenoid valves 34 and 35, connected to the micro-bioreactors 41–48 respectively, are connected to a processing unit 5 comprising a central processing unit 8 comprising a microcomputer coupled to an analog/digital and digital/analog interface system.

A first diagram for an embodiment of the electronics of a turbidity measurement apparatus, represented in FIG. 9, is applicable to an isolated micro-bioreactor or a micro-bioreactor in a battery.

In the electronics diagram, the earth is given the reference 80 and the operational amplifiers have negative and positive input terminals and output terminals referenced A, B and C respectively.

The symmetric supply is preferably stabilised and regulated to a voltage +V equal to +12 Volts and −V equal to −12 Volts.

In addition, all the fixed resistors are for example ¼ W metal film type and the condensers are non-polarised. The values of the variable resistors and potentiometers for 10 turns −½ W are given elsewhere.

The light source 3 comprises an infrared electroluminescent diode 73 or LED, and the photodetector 4 comprises a phototransistor 74 of Darlington type. This phototransistor 74 is provided with a 0.1 $\mu$F condenser C1, to prevent oscillations.

The control unit 6 comprises an operational amplifier 81, whose positive input B receives a controlled voltage and whose negative input A is connected to earth 80 via the resistor R1. The output C of amplifier 81 controls, via a transistor 87 acting as a buffer device, the intensity of the current 11 passing through the diode 73, and thus the intensity of the transmitted beam 11. The gain of the amplifier 81 is fixed at 2 by the resistors R1 and R3, each of 1 k$\Omega$. The control unit 6 also comprises a resistor R5 of 90.9 $\Omega$, at the terminals of which the voltage U1 is measured. This resistor R5 fulfils the function of a current/voltage converter and limits the maximum current passing through the diode 73 to 100 mA.

The control unit 6 also comprises two resistors R2 and R4 of 1 k$\Omega$ and 100 $\Omega$ respectively.

The feedback regulating system 7 comprises a resistor R6 of 1 k$\Omega$, which converts the intensity I2 leaving the phototransistor 74 into the voltage U2. The feedback regulating system 7 also comprises an operational amplifier 82, whose negative input A receives this voltage U2, whose positive input B receives the reference value V2 and whose output C is connected to the positive input B of the amplifier 81 of the control unit 6. The gain of the amplifier 82 is very high because it does not have a negative feedback resistor, and thus has high sensitivity to the intensity variations of the transmitted beam 12, giving a high efficiency of feedback control. The amplifier 82 is provided with a 1 $\mu$F condenser C2, to prevent oscillations.

The regulating system 7 also comprises a resistor R7 of 1 k$\Omega$, connected to the positive input B of amplifier 82.

In the example illustrated, the processing unit 5 is made, on the one hand, of a current/voltage converter stage 72, connected to the unit 7, a voltage/current converter stage 71 connected to the unit 6, and on the other hand a central processing unit 8 made of a microcomputer provided with an analog/digital, digital/analog conversion interface communicating by a 4–20 mA current loop. This latter type of communication by current loop makes stages 71 and 72 necessary. A computer system provided with a converter card working directly on voltage makes stages 71 and 72 unnecessary.

The converter stage 71 is based on the use of an operational amplifier 83, whose positive input B receives the voltage U1, and on a voltage/current converter circuit 84, whose input is connected to the output C of the amplifier 83. The converter stage 71 also comprises the resistors R80–R12 with values 2.43 k$\Omega$, 2,43 k$\Omega$, 1 k$\Omega$, 1 k$\Omega$ and 2.25 k$\Omega$ respectively. It also comprises a potentiometer P1 of 200 $\Omega$, an adjustable resistor P2 of 50 $\Omega$ and a condenser C3 of 1 $\mu$F.

The converter stage 72 is based on the use of two operational amplifiers 85 and 86. The positive input B of the amplifier 85 receives a voltage from the central processing unit 8, representative of the reference value V2. The output C of the amplifier 85 is connected to the positive input B of the amplifier 86 and the output C of the amplifier 86 is connected to the positive input B of the amplifier 82 of the feedback regulating system 7. The processing unit 5 thus sends the reference value V2 to the feedback regulating system 7, which enables an order to change the measurement range to be given, if necessary.

The converter stage 72 also comprises resistors R13–R20, the resistors R14–R16, R19 and R20 being of 1 k$\Omega$, and the resistors R13, R17 and R18 being of 250 $\Omega$, 1.3 k$\Omega$ and 1.82 k$\Omega$ respectively. The converter stage 72 also comprises a potentiometer P3 of 500 $\Omega$, an adjustable resistor P4 of 1 k$\Omega$ and condensers C4 and C5 each of 1 $\mu$F.

The processing unit 5 advantageously comprises a control unit, designed to control the opening and closing of the various solenoid valves included in the circuits for supplying the culture medium 15 and also the sterile air or gas 14. For example, the processing unit 5 acts on the solenoid valves 34 and 35 of the micro-bioreactors 41–48 via the control systems 91–98 respectively.

As an example of an embodiment, the diode 73 and phototransistor 74 are manufactured by Honeywell and marketed under the names SE5470-003 and SD5410-002 and the operational amplifiers 81, 82, 83, 85 and 86 are manufactured and marketed under the name LM358A by National Semi Conductors (NSC). The converter circuit 84 is of type 2B20A manufactured by Analog Devices (AD) while the transistor 87 is marketed under the reference 2N2222.

According to a second embodiment of the electronics (FIG. 10), the stages 71 and 72 are avoided by use of an electronic card, which performs the analog/digital and digital/analog conversions directly and communicates the results in digital form via a communication bus.

The voltage U1 at the terminals of the resistor R5 is thus transmitted to the card in the form of an analog signal by an output point PT1. In addition, the positive input B of the operational amplifier 82 is connected to the card via resistor R7, by an input point PT2. The card thus communicates the reference value V2 in analog form to the regulating system 7.

According to a third embodiment of the electronics (FIG. 11), an alternative of the second embodiment, the negative input A of the operational amplifier 82 is also connected to the card, by a control point PT3. This point PT3, which allows transmission of the value of the voltage U2, is designed to check the correct operation of the voltage adjustment and the feedback. It thus makes possible, by identifying the differences between the voltages U2 and V2, an overall control of all the components of the whole assembly.

All the components of the control unit 6 and the regulating system 7 are preferably installed on an electronic card or board.

Advantageously, several cards, including a specific initialisation card, are integrated in a casing.

In operation, it is advantageous to proceed as described below for any one of the micro-bioreactors 41–48 of the battery 40, the micro-bioreactors being independent from each other since they are controlled by a separate computer program. At regular intervals, a time counter starts and when the time is equal to a fixed value, the following actions are triggered:

A signal is sent by the program of the central processing unit 8 which thus triggers, via a relay (control systems 91–98), the solenoid valve 34; this interrupts the passage of sterile air or gas into the micro-bioreactors 41–48 so as not to cause bubbles, which cause measurement errors.

This program also inserts the reference value V2 into the feedback regulating system 7.

The reference value V2 being fixed, the feedback regulating system 7, operating independently, adjusts the voltage U1 to transmit the exact quantity of light which, after passing through the tube 2, causes the appearance of a voltage U2 equal to the reference value V2 and proportional to the current 12 passing through the photodetector 4.

The value of the voltage U1 is converted into a digital value and recorded by the program.

The couple light source 3—photodetector 4 is returned to a standby status.

The closing of the solenoid valve 34 re-establishes aeration or the passage of gas.

The time counter is reset to zero.

If the measured value of U1 does not exceed certain fixed threshold values, the program calculates the corresponding value of the turbidity T, by using an equation previously determined empirically. For each value of the reference value V2 there is a corresponding equation, for example of the form:

$$T = a \times U1^3 + b \times U1^2 + c \times U1 + d,$$

where the coefficients a, b, c, d are determined experimentally for the value of V2.

The cycle recommences.

If the measured value of U1 exceeds the fixed threshold, a lower value of the reference value V2 is then selected and the time counter is incremented artificially so that the measurement is immediately retaken with this new parameter, then the turbidity T is calculated.

The cycle recommences.

The values of the turbidity T are displayed on the microcomputer screen of the central processing unit 8, which allows the development of the culture to be monitored over time. These values are also stored in a file, so that the data may be processed later, for example in a spreadsheet.

In an alternative of this embodiment, the measurements are made in bursts. The use of the solenoid valve 34 thus becomes unnecessary.

It is advantageous that the procedure described above is used for automating cyclic cultures. In an advantageous embodiment, a control algorithm determines the growth of the cell population by performing a linear regression calculation on the n latest values of turbidity T measured, n being adjustable. The slope of the regression line obtained is calculated: if it is less than or equal to a fixed value, the population growth is considered as zero and the counter is started. If the culture resumes growth, for example after a phase of diauxie, the counter is reset to zero. When the counter reaches a fixed value, the program in the central processing unit 8 triggers the opening of the relevant solenoid valve 35, via the interfaces, which supplies fresh culture medium for a fixed time, so as to perform an exponential dilution. The measurement cycles then recommence.

Figure 13:
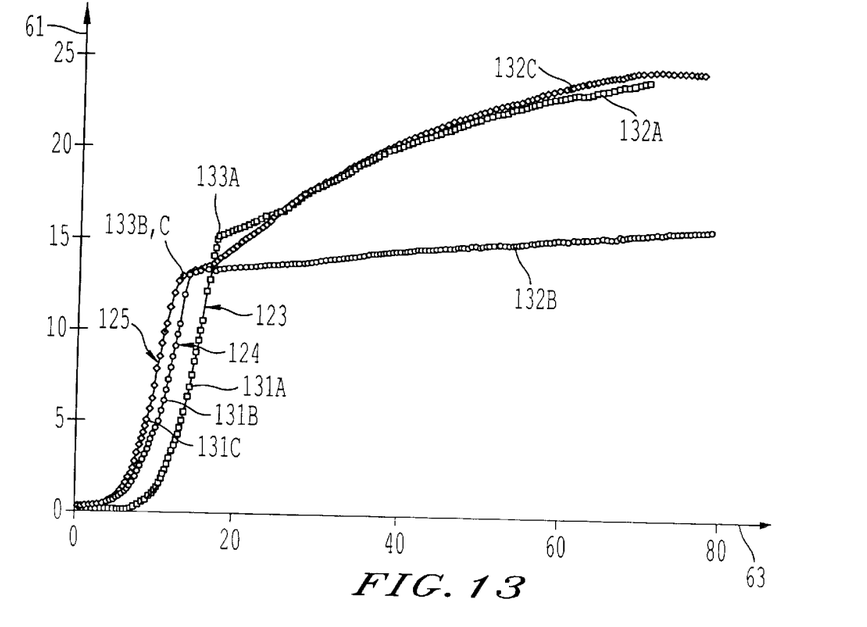
FIG. 13 shows the growth curves, giving the development of the turbidity, as a function of time, expressed in hours, of three strains of *Saccharomyces cerevisiae*, respectively types FY23, FY73 and FY1679, cultivated in YPD complex medium (yeast extract, peptone, glucose) at 30° C., obtained with a measurement apparatus according to the invention.
Figure 14:
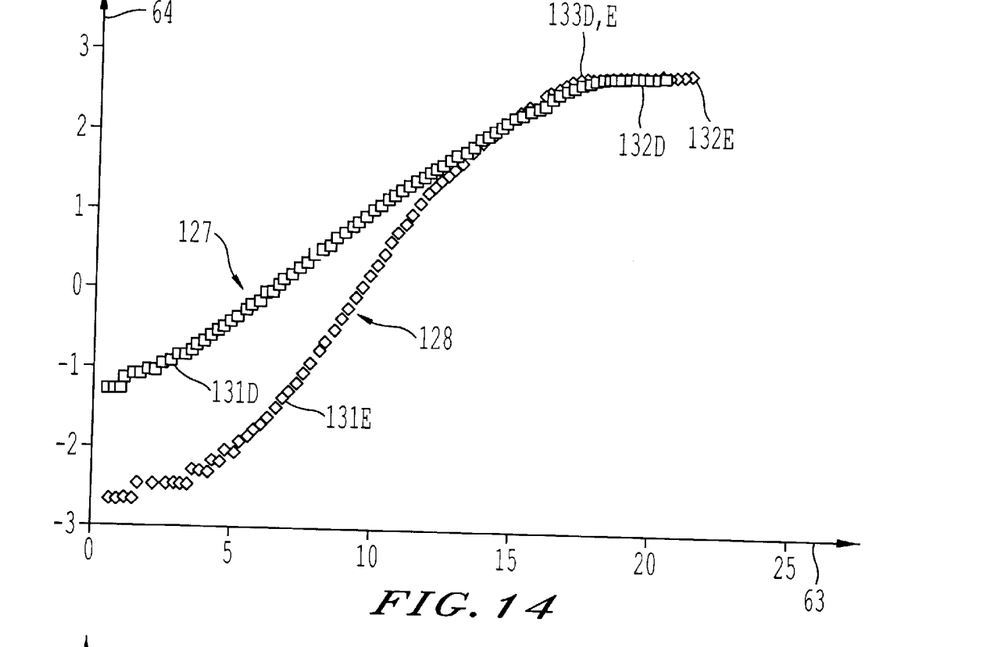
FIG. 14 shows in parallel the growth curves (Napierian logarithm of the turbidity as a function of time in hours) of strain type FY23 and the mutant of type FYBL2-5D/Dn049, cultivated in YPD complex medium at 30° C., obtained with a measurement apparatus according to the invention.
Figure 15:
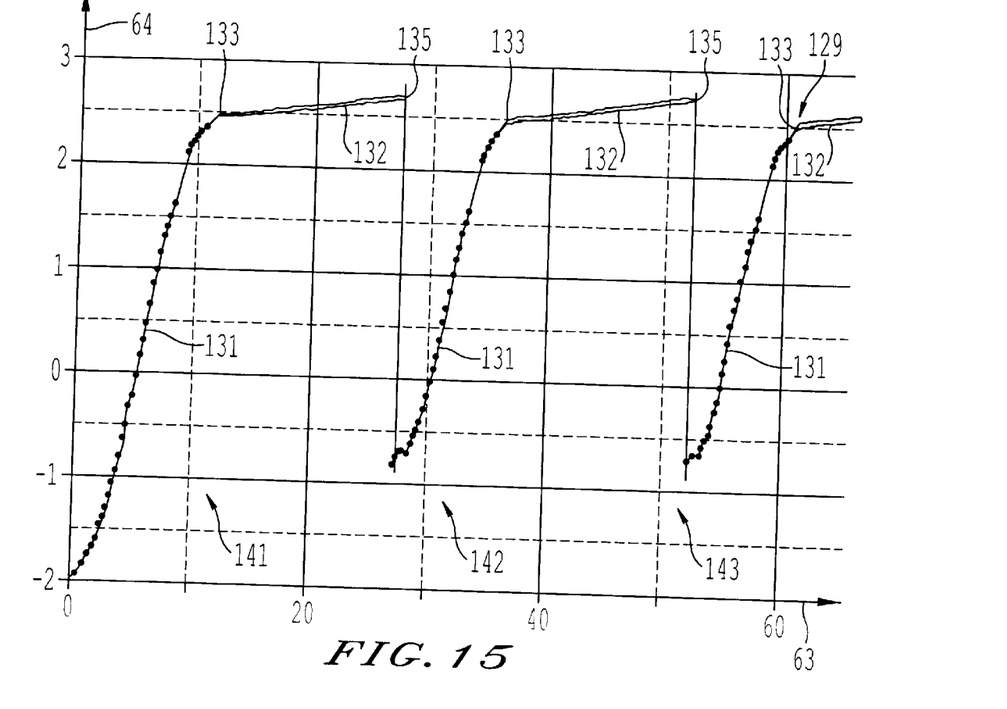
FIG. 15 shows the growth curve in automated cyclic culture of strain type FY1679 cultivated in YPD complex medium at 30° C., obtained with a measurement apparatus according to the invention.

Various results obtained with a micro-bioreactor equipped with a turbidity measurement apparatus as described above are mentioned below. Growth curves were obtained from strains of the yeast *Saccharomyces cerevisiae* cultivated in YPD complex medium at 30° C. The results obtained, shown on FIGS. 13 to 15, show an excellent homogeneity of the values, in other words very little dispersion, and differences of the order of 2% compared to measurements performed in parallel with a spectrophotometer on samples removed from these cultures. Because of its reliability, the turbidity measurement apparatus may thus be used very easily to compare the growth of the strains.

In general, the growth curves, which give the turbidity T as a function of time, each contain a part 131 with a high rate (steep slope) of growth followed by a part 132 with low growth rate (shallow slope), separated by a plateau 133. The curves of cultures of the wild strains FY23, FY73 and FY1679, respectively referenced 123, 124 and 125 and plotted on FIG. 13 against a time axis 63 (in hours) and a turbidity axis 61 (in OD units), have respectively parts with high growth rate 131A, 131B and 131C, parts with low growth rate 132A, 132B and 132C and transition plateaux 133A, 133B and 133C.

Comparison of these growth curves 123–125 shows that strain FY73, after having consumed all the glucose in the medium, grows very slowly on the ethanol produced by fermentation of the glucose. In contrast, strains FY23 and FY1679 have a faster growth on ethanol (parts with shallow slope 132A and 132C). In addition, the plateaux 133B and 133C of diauxie of the strains FY73 and FY1679 are initiated at a lower turbidity (at 12.8 OD units) than the plateau 133A of strain FY23 (at 14.8 OD units).

Other results, shown on FIG. 14 against a time axis 63 (in hours) and an axis 64 giving the Napierian logarithm of the turbidity T (in OD units), represent the growth curves 127 and 128 of the mutant FYBL2-5D/Dn049 and strain FY23, respectively. Curves 127 and 128 respectively contain parts of high growth rate 131D and 131E, parts of low growth rate 132D and 132E and transition plateaux 133D and 133E. It may be seen that strain FY23 has a growth rate of 0.545 h$^{-1}$, which is almost twice the growth rate of strain FYBL2-5D/Dn049, of 0.286 h$^{-1}$.

A growth curve 129 of a cyclic culture of FY1679 whose dilutions were completely controlled by microcomputer, shown on FIG. 15, contains a succession of similar cycles 141–143. Each of these cycles comprises a part of high growth rate 131 and a part of low growth rate 132, separated by a transition plateau 133. The dilution was started at a dilution point 135, 24 hours after the start of culture. The dilution may also be started when the growth rate has become close to zero, or after a certain length of the stationary phase of the culture.

In another embodiment, the measurement apparatus comprises:

a light source/light detector couple integrated into the apparatus, an interface device comprising a bus for data circulation between an automatic data processing device and one or more measurement units, and relays, an automatic data processing device, such as a microcomputer, provided with electronic cards which can control the data flow within a data bus and an electronic card or software able to process the collected data mathematically.

The measurement unit or units advantageously comprise one or more relay cards, designed to activate the solenoid valves, and one or more measurement cards. The latter comprise:

a measurement system connected to the light source and the detector, a digital/analog converter allowing processing of the data coming from the bus and thus fixing a suitable voltage to be applied to the light source so as to maintain the reference voltage of the detector.

A measurement unit advantageously comprises, for example, ten measurement cards and five relay cards, each of the measurement cards being connected to a micro-bioreactor and the relay cards being connected to the solenoid valves.

What is claimed is:

1. Apparatus for determining at least one optical property of a medium, comprising:
   a light source configured to provide a transmitted beam that is transmitted towards and into the medium;
   a detector configured to measure intensity of a modified beam exiting from the medium,
   a control unit configured to control the intensity of the beam transmitted by the light source,
   a processing unit configured to provide a representative value of a nominal intensity of the modified beam, and
   a feedback regulating system linked to the control unit, the detector, and the processing unit, and configured to control operation of the control unit so that the measured intensity of the modified beam is made equal to the nominal intensity to establish a stabilised intensity for the transmitted beam,
   wherein the processing unit is further configured to adjust the representative value of the nominal intensity so that the stabilised intensity of the transmitted beam falls within a predetermined range.

2. The apparatus according to claim 1, wherein the processing unit includes a storage unit designed to store a saturation intensity and to adjust the representative value of the nominal intensity to a lower value when the stabilised intensity of the transmitted beam is higher than the saturation intensity.

3. The apparatus according to claims 1 or 2, wherein the light source and/or the detection means are designed to measure the intensity of the modified beam around at least one wavelength corresponding to said at least one optical property.

4. The apparatus according to claim 1, wherein said at least one optical property comprises turbidity.

5. The apparatus according to claim 4, wherein the light source and/or the detection means have a wavelength around 880 nm.

6. The apparatus according to claim 1, wherein said at least one optical property comprises absorbance.

7. The apparatus according to claim 1, wherein said at least one optical property comprises fluorescence.

8. The apparatus according to claim 1 further comprising a storage device configured to store at least one equation determined by a calibration curve giving said at least one optical property as a function of the intensity of the transmitted beam for at least one respective value of the intensity of the modified light beam wherein the processing unit calculates said optical property from the stabilised intensity of the transmitted light beam for said at least one respective value of the nominal intensity and the equation.

9. The apparatus according to claim 8, wherein the processing unit comprises a central processing unit and at least one card configured to provide analogue/digital and digital/analogue conversion and to couple the central processing unit to the control unit and the feedback regulating system.

10. The apparatus according to claim 1, further comprising a clock, a recording unit, and a repeated activation unit configured to repeatedly activate the feedback regulating system and the recording unit.

11. The apparatus according to claim 1, wherein the feedback regulating system and the control unit are configured to provide continuous equalisation of the measured intensity and the nominal intensity of the modified beam.

12. Micro-bioreactor (20, 41–48) including an apparatus according to claim 1.

13. Micro-bioreactor according to claim 12, further comprising:
   a tube closed by a stopper configured to contain a culture,
   a first pipe configured to inject sterile air or gas and a culture medium into the culture, and
   a second pipe, configured to remove effluents, wherein the tube and the pipes are under pressure.

14. Micro-bioreactor according to claim 13, further comprising a dilutation system designed to dilute the culture on a cyclic basis controlled by the processing unit.

15. Micro-bioreactor according to claim 14, wherein the processing unit repeatedly activates the feedback regulating system, records representative values of said at least one optical property in a storage unit, and triggers the dilution system when a stagnation of said at least one optical property over a plurality of the latest recorded values is observed.

16. Micro-bioreactor according to claim 13 wherein, at least one of the pipes includes a connector comprising a male part female part, a connection part configured to connect said male part and said female part together, each of said male and female parts comprising:
   a tapered hollow end configured to be connected to one end portion of said at least one of the pipes, and
   a sleeve surrounding a coupling hollow part communicating with said tapered hollow end, the coupling hollow part of the male part being introduced into the coupling hollow part of the female part, with the sleeve of one of the parts being introduced into the sleeve of the other part so that said sleeves are connected to each other by the connection part.

17. Micro-bioreactor according to claim 16, wherein the sleeve of the male part is introduced into the sleeve of the female part.

18. Micro-bioreactor according to claim 16, wherein the connection part includes a locking ring.

* * * * *